United States Patent [19]

Entwistle

[11] Patent Number: 4,668,346
[45] Date of Patent: May 26, 1987

[54] ION CONCENTRATION ANALYSIS AND APPARATUS EMPLOYING STANDARD ADDITION TECHNIQUES

[75] Inventor: James R. Entwistle, Bolton, England

[73] Assignee: British Nuclear Fuels plc, England

[21] Appl. No.: 842,249

[22] Filed: Mar. 21, 1986

[30] Foreign Application Priority Data

Oct. 22, 1985 [EP] European Pat. Off. ........ 85307602.4

[51] Int. Cl.[4] ...................... G01N 27/28; G01N 27/46
[52] U.S. Cl. ................................... 204/1 T; 204/401;
204/402; 204/416; 422/68; 436/43; 436/174
[58] Field of Search ............... 204/402, 401, 416, 1 T;
436/43, 174; 422/68, 81

[56] References Cited

U.S. PATENT DOCUMENTS

| 4,151,255 | 4/1979 | Capuano et al. | 422/76 |
| 4,236,988 | 12/1980 | Suzuki et al. | 204/402 |
| 4,512,852 | 4/1985 | Tsuboshima et al. | 204/1 T |
| 4,600,494 | 7/1986 | Bromberg et al. | 204/401 |

FOREIGN PATENT DOCUMENTS

| 3230327 | 12/1982 | Fed. Rep. of Germany | 204/1 T |
| 2482306 | 11/1981 | France | 204/1 T |
| 2157438 | 10/1985 | United Kingdom | 204/1 T |

OTHER PUBLICATIONS

Karl Cammann, "Working with Ion-Selective Electrodes", pp. 137-147 (1979).
Ullmanns Encyklopadie der Technishen Chemie, vol. 5, 4th edition, pp. 655-658, Verlag Chemie, Weinheim (1980).
Ion-Selective Electrode Methodology, vol. I, editor Arthur K. Covington, pp. 43-66 (1984).

Primary Examiner—G. L. Kaplan
Attorney, Agent, or Firm—Larson and Taylor

[57] ABSTRACT

Analysis of a series of samples is carried in an electrode cell (10) containing an ion-selective electrode (11). A base solution, to which a trace of the ion to be measured has previously been added, is run into the cell (10). To perform an analysis a small volume of solution, containing a known concentration of the ion is added, followed by an identical volume of sample. The pX or mV measurement before and after each of the two additions is recorded and the analytical result calculated. After analyzing the first sample, the cell is drained, without rinsing and the second sample analyzed in the same way. No blank determination is required. In more sophisticated versions of the technique, at least two additions of standard are made, one before and one after the sample.

12 Claims, 2 Drawing Figures

ION CONCENTRATION ANALYSIS AND APPARATUS EMPLOYING STANDARD ADDITION TECHNIQUES

This invention relates to ion concentration analysis using an ion-selective electrode and is directed to an improved incremental addition technique which can considerably speed and simplify such analysis and most importantly can markedly improve precision and accuracy.

By ion concentration is meant the total ionic concentration, free and chemically complexed, present in the sample solution.

In accordance with one aspect of the present invention (herein called the basic procedure) a method of making an analysis of ion concentration in a series of samples using an ion-selective electrode in an electrode cell comprises the steps of:

(a) filling the cell with an approximately known volume of base solution doped with a trace of the ion to be determined, and taking an initial reading of the electrode potential;

(b) adding from a dispenser a volume of liquid (herein called the standard solution), small relative to the volume of the base solution, containing a known concentration of the ion to be measured;

(c) recording the changed electrode potential;

(d) adding a volume of the first sample for analysis, which volume may be the same as in (b) or have a known proportional relation with said volume of standard solution;

(e) recording the new electrode potential;

(f) draining the cell such as by suction without rinsing;

(g) proceeding back to (a) above for the next sample analysis; and (h) calculating the results of the analysis from the recorded values of the electrode potential.

Certain amplifications of the basic steps are given below:

(i) The order of additions (b) and (d) can be exchanged for some applications. Also one or more further additions (b) and/or (d)—herein called the multi-addition procedure—can be made to eliminate the need to know the electrode slope. If more than one addition of standard solution is made either a larger volume of the same standard solution can be used or (preferably) the same volume of a more concentrated standard solution can be used. In a preferred form of the invention, additions of the standard solution are made prior to and after addition of the sample, the same volume preferably being used for each addition and the concentration of the second standard solution being higher than the first (typically 5 times greater).

(ii) The additions in (b) and (d) may be made using plastic-tipped microlite pipetes. The volume delivered by the pipette is typically between 0.1 and 1% of the volume of the base solution, depending upon the application. If the identical pipette is used for the additions in (b) and (d), any inaccuracy in the nominal volume of the pipette is of no consequence. Corrections are made in the calculations for volume changes caused by the additions.

(iii) For maximum precision and accuracy, weighing of the standard and sample additions is advantageous, especially with the multi-addition procedure. This is particularly useful when a weighed solid sample is dissolved to give a known weight of solution from which the sample addition is made.

(iv) There is no blank determination, this being corrected for inherently in the procedure.

(v) If a pX measurement is made, either a temperature compensation probe can be included in the cell, or the temperature can be recorded manually and adjusted on the pX meter. If mV measurements are taken the temperature of the solution must be recorded. The use of a temperature probe is not essential in the multi-addition procedure.

(vi) After step (f) when the analysis of a sample is completed, there is no requirement to rinse the electrodes and cell before proceeding back to step (a). Any residual analyte is determined by addition step (b) and is automatically compensated for in the calculation.

(vii) The composition of the base solution, which has a typical volume of 20–100 ml, depends on the analyte and type of sample analysed, and is based on general chemical principles. However, it must always have the properties stated below:

(A) it must be doped with a relatively low concentration, which need be known only very approximately, of the analyte to be determined. This concentration must be on the linear response range (electrode potential vs $\log_{10}$ (concentration or activity)) of the electrode, be high enough to give a reasonably rapid response time, and give convenient pX/mV changes when the additions are made, (B) it must have an ionic strength background that is not significantly changed by addition of the sample/standard solutions. This can be achieved either by including in the base solution a component which provides a relatively high ionic strength background which is effectively unchanged when relatively small volume additions of standard and sample solutions are made or by adjusting the ionic strength background of the base solution to a level similar to the ionic strength of the sample and standard solutions.

(C) it must contain chemical components which mask any interfering ions present in the samples and to which the electrode may respond to some degree. In addition it is sometimes necessary that the base material forms a chemical complex with the measured ion so that only a small constant fraction of the latter is available to be sensed by the electrode.

(D) in addition species which chemically complex the analyte may, of necessity, be present in the sample. In this event the base solution must contain a sufficient excess of the same or a different complexing agent to ensure that the ratio total analyte concentration to free analyte ion concentration (as sensed by the electrode) is constant. However this ratio may decrease slightly but significantly in value as additions are made to the base solution, especially when analysing a sample with a high analyte concentration. Such small decreases can be corrected for in the calculation.

(viii) The following parts of the procedure may, if desired, be microprocessor controlled using available technology; (1) the filling and draining of the electrode cell, (2) automatic storage of measurements, when these are stable to any predetermined criterion and (3) calculations of the analytical results. Extension to the automatic additions of standard and sample is also feasible.

The advantages of the procedure, compared with conventional ion-selective electrode methodology, and microprocessor-controlled units to aid such conventional analysis, are given below:

(a) There is no blank determination.

(b) For liquid samples no additional plastic/glass containers, other than the electrode cell, are required, any number of analysis being possible in the same cell.

(c) No cleaning/rinsing of the electrode and cell is required before, after and during a series of sample analyses.

(d) For liquid samples contamination problems are virtually eliminated. The only possible source of contamination, other than from the air is from the micropipette tips. When a previously unused tip is used for each addition, the risk of contamination is negligible, and no special precautions to prevent it are required.

(e) Because of (a) to (d) immediately above, analyses are frequently faster and require much less skill than conventional ion selective electrode methods, virtually the only skill required being the correct use of the micropipette. An analysis takes typically between 1 and 5 minutes, and depends primarily on the response time of the electrode at the analyte concentrations measured. For liquid samples, there is no additional preparation time, or delay time between consecutive analyses.

(f) There is frequently better electrode performance. This occurs because the electrode is always immersed in the base solution, the composition of which only changes marginally. Thus the electrode becomes permanently 'conditioned' to a particular solution, resulting in better stability and faster response time.

(g) In contrast to most conventional known addition methods, a low sample concentration is associated with a small potential change, and a high concentration with a high change. Thus the response is (very approximately) linear with concentration. This is intuitively more satisfactory.

(h) The problem of determining whether the sample concentration will bring the measured solution on to the linear response range of the electrode does not exist, as the base solution is previously doped to ensure this.

(i) For the basic procedure, identical additions can be used to cover a very wide concentration range, typically about 1000-fold, from the limit of detection to the upper limit.

(j) The selectivity coefficient for an interferring ion is very simply determined by substituting a solution of the interferring ion, of known concentration, for the sample solution.

(k) Notwithstanding the frequently convenient small sample aliquot required, relative to conventional standard addition procedures, sample limits of detection are surprisingly low for the basic procedure, and are typically similar to the analytic concentration of the base solution. This is because of the high reproducibility of the small potential change which occurs when the sample addition, for a sample of low analyte concentration, is made, volume corrections being applied.

(l) The precision of the basic procedure is usually better than with conventional procedures, the accuracy being similar. For the multi-addition procedure however, especially in the preferred form, precision and accuracy are much superior to conventional techniques. The precision of the preferred procedure, when standard and sample additions are both weighed, is comparable to a conventional titration procedure with a good end-point, and superior to titrations with inferior end-points. The amount of sample is much less than required for a conventional titration. Also the problem of finding a suitable titrant for 'difficult' analytes (eg nitrate) and the problem of end-point detection are both eliminated. Thus the procedure can be used when a titration procedure cannot be devised. The preferred procedure is also much superior in precision and accuracy to other multi-addition procedures (eg the Gran plot) primarily because the sample concentration is obtained by "bracketting" with standards rather than by extrapolation.

According to a second aspect of the invention there is provided apparatus for determining ion concentration in a series of samples, comprising an electrode cell, an ion selective electrode located in the cell, means for registering the output of the electrode, means for supplying an at least approximately known volume of a base solution to the cell, the base solution is use being doped with a trace of the ion with respect to which the electrode is selective, means for supplying to the cell a volume of liquid (herein called the standard solution), small relative to the volume of the base solution and containing a known concentration of said ion, means for supplying to the cell one of said samples in a volume related to that of the standard solution, means for draining the contents of the cell, and control means for effecting cyclical operation of the registering means, supplying means and the draining means in such a way that, during each cycle, the base solution is initially added to the cell and is followed by successive additions of the standard and sample solutions in a predetermined order, the registering means being operable to record the output of the electrode after each such addition to the cell and the draining means being operated to empty the cell in preparation for the next cycle, the control means including means for computing from said recorded outputs the ion concentration for each sample.

Figure 1:
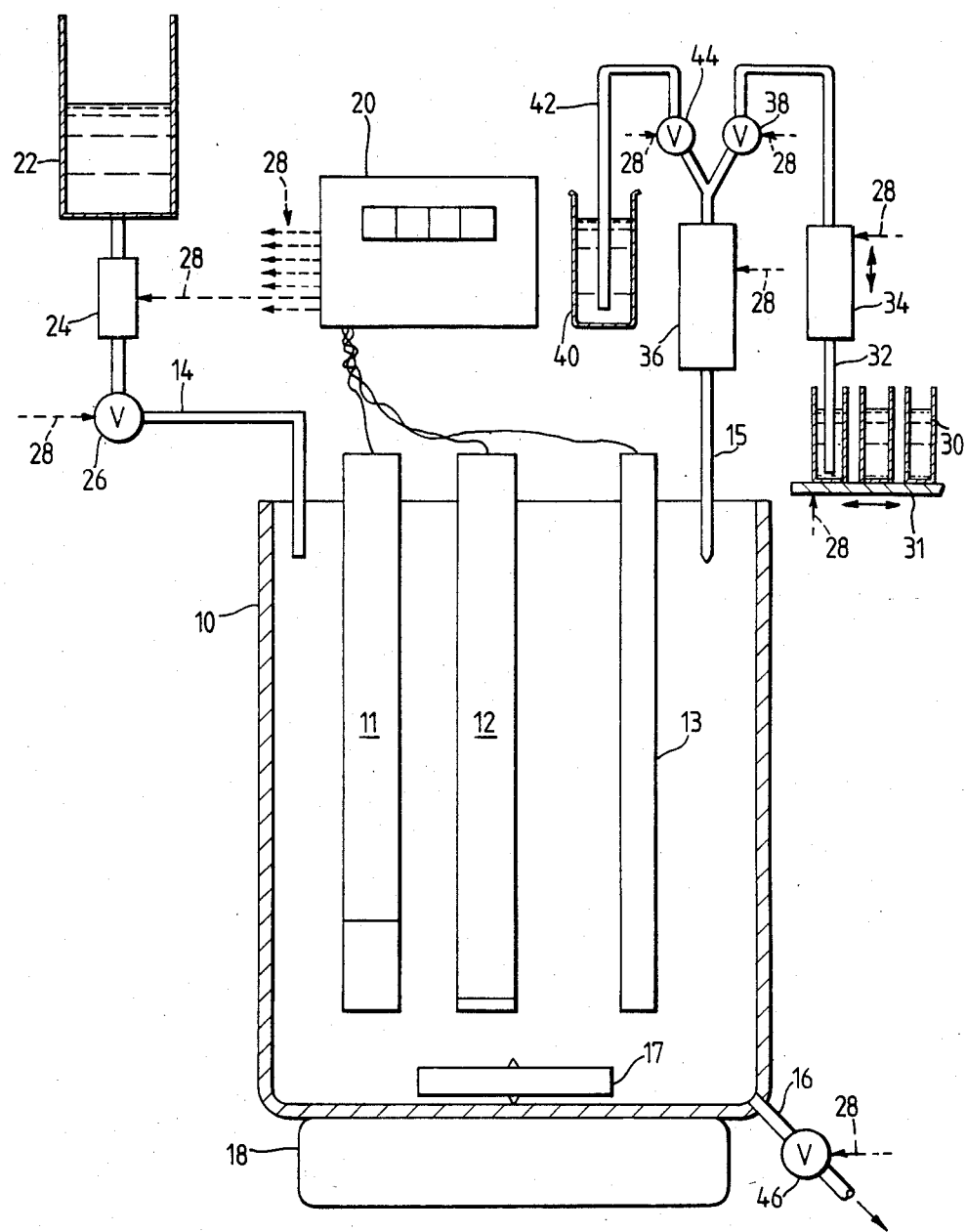
FIG. 1 is a diagrammatic representation of the apparatus of the invention.

The invention will now be described further with reference to FIG. 1 of the diagrammatic accompanying drawing which is not to scale.

In the drawing there is shown an electrode cell 10, with an ion-selective electrode 11 and reference electrode 12 connected to a pX/mV meter of a microprocessor-based control unit 20. A combination ion-selective electrode can replace the electrodes 11, 12 if desired. Also connected to the pX/mV meter or microprocessor is an automatic temperature compensator 13, but a manually read thermometer can replace this. The cell has an inlet 14 for the base solution contained in storage vessel 22 and an inlet 15 for adding the standard solution and the sample to be analysed. An outlet 16 is provided and the cell contains a magnetic stirrer bar 17, actuated by a magnetic stirrer motor 18 beneath the cell.

The base solution is supplied to the cell 10 by means of a volume measuring dispenser 24 and valve 26 which are controlled by the microprocessor-based unit 20 (as indicated by connections 28) so as to deliver a known volume (typically 50 ml) of the base solution to the cell at a predetermined point in the cycle of operation. The samples are typically made available in a series of test tubes 30 carried by some form of transport mechanism 31 such as a carousel for moving or indexing the samples successively into registry with a sampling pipe 32 insertable into the sample tubes by a raising and lowering device 34. The sampling pipe 32 is connected to an automatically operable pipetting device 36 of which the inlet 15 may form part. A valve 38 controls the connection between the pipe 32 and pipetting device 36.

The standard solution contained in vessel 40 is also introduced into the cell by way of the pipetting device 36, pipe 42 and valve 44. The pipetting device 36 when operated serves to draw up a predetermined volume of standard or sample solution, according to which of the valves 38, 44 is open, and dispense it into the cell 10. As indicated by connections 28, the pipetting device 36, the valves 38, 44, the carousel 31, the device 34 are all controlled by the control unit 20 so as to operate in a predetermined sequence. Likewise the outlet 16 is provided with a valve 46 controlled by the unit. A means of rinsing the pipetting/dispensing system between samples may also be provided.

As an alternative to the pipetting/dispensing system described the whole operation of making additions of sample and standard to the base solution can be performed by a robot arm.

In use, with the stirrer 17 operational, the sequence of operation comprises introducing a known volume (the precise volume need not be known) of base solution into the cell by opening valve 26 and operating dispenser 24. The valve 26 is then closed and after the pX/mV meter reading has become stable, the electrode output value is recorded in memory storage of the control unit 20. The next step may comprise the addition of standard solution to the cell by operation of pipetting device 36 accompanied by opening of valve 44. Again after a stable electrode output has been obtained, the value is recorded in storage. The first sample is now introduced into the cell 10 by operation of pipetting device 36 accompanied by opening of the valve 36 (valve 44 having been closed in the meantime). The stable electrode reading is recorded in storage and the value for the ion concentration in the sample can be computed and recorded. Before proceeding to the next sample, the valve 46 is opened to drain the cell 10 and the device 34 and transport mechanism are operated to bring the next sample into position for analysis. The cycle is then repeated for each successive sample.

Among many other applications the basic procedure is very useful for the rapid determination of acids and alkalis, at virtually any concentration in any type of sample, the analysis being particularly fast (about 1½ minutes). The preferred form of the multi-addition procedure can also be used for results of high accuracy and precision. The basic procedure may be illustrated in the context of determining free nitric acid in uranyl nitrate solutions which is usually performed, with some difficulty, by titration. Here the problem of hydrolysis of the uranyl ion is eliminated by complexing uranyl ion with sulphate at a pH less than or equal to 3.0 under which conditions hydrolysis of uranyl is insignificant. The ion-selective electrode used is a combination glass electrode, and an automatic temperature compensator may be present.

A base solution, consisting of approximately 50 ml of magnesium sulphate solution (2.5M), doped with about 100 mg/l nitric acid to give a pH of approximately 3.3 is used. This is supplied to the electrode cell and stirred. When the electrode potential is stable, the reading (mV or px) is recorded and stored.

A standard solution of 0.2 ml of nitric acid (0.5M) is then added. This constitutes a known amount of the ion to be measured. Stirring is continued and a further stable electrode potential reading is taken and stored. The same volume (0.2 ml) of sample is now added from the pipetting device, and the new stable electrode potential reading then taken.

The % w/v nitric acid in the sample can then be calculated in the manner described hereinafter.

After taking the electrode potential reading following addition of the sample the stirrer 17 can be stopped and the cell drained. There is no need to rinse the electrodes or the cell before dealing with the next sample. Also, if the same pipette is used for the standard and sample additions, an exact knowledge of the pipette volume is not essential.

It is to be observed that in the above procedure hydrogen ion is also complexed by sulphate as the bisulphate ion ($HSO_4^-$) and only a fraction of the total hydrogen ion is sensed by the electrode. The philosophy of the procedure and composition of the base solution ensures, however, that the total hydrogen ion concentration is determined. This is because the same fraction of total hydrogen ion concentration present in the standard and sample solutions, is measured in both cases. The above procedure, using the doped magnesium sulphate solution, can also be used to determine the strength of any dilute mineral acid solution (of approximately 0.0015–5M).

Another example illustrating the invention is the measurement of nitrate ion concentration in effluents. Ion selective electrodes responsive to the nitrate ion are available commercially from Orion Research Incorporated, 380 Putnam Avenue, Cambridge, Mass., USA. However, commercially available nitrate ISE's tend to respond also to chloride ions, which is undesirable. The base solution employed for nitrate ion analysis may therefore include a component such as silver oxide which will complex with any chloride present to give insoluble silver chloride and thereby mask any chloride activity that would otherwise be detected by the ISE. In addition, the base solution incorporates ammonium fluoride, which affords a constant ionic strength background that will be substantially unaffected by subsequent standard and sample solution additions, buffers acidic samples and is doped with a low concentration of the nitrate ion (which may be introduced by the addition of sodium nitrate) so as to bring the ISE into the linear part of its response.

A further example illustrating the invention is the measurement of fluorine ion in $UF_4$ using the preferred form of multi-addition procedure. In this case, about 0.5 g of accurately weighed $UF_4$ is initially dissolved in 0.18M ferric nitrate/3M nitric acid, in a sealed plastic vessel, to form the sample solution (which contains uranyl ions) which is weighed. The base solution comprises 0.2M ferric nitrate/0.8M nitric acid doped with 5 milligrams per liter of fluoride, eg. sodium fluoride. The ferric nitrate/nitric acid in the base solution provides a substantially constant ionic concentration background and the ferric ion is also a suitably strong fluoride complexant to effectively "swamp out" complexation due to uranyl and hydrogen ions and provide a constant degree of complexation in the base solution, the ISE responding only to the residual uncomplexed fluoride ions present. The standard solutions in this case may be sodium fluoride in a simulated base solution (ferric nitrate/nitric acid) intended to maintain a constant ionic strength and degree of complexation. In this case, using the multi-addition procedure, a first (weighed) 0.2 ml portion of standard solution is added to 50 ml base solution, then the (weighed) 0.2 ml sample solution, followed by a second (weighed) 0.2 ml standard solution, as explained previously.

Figure 2:
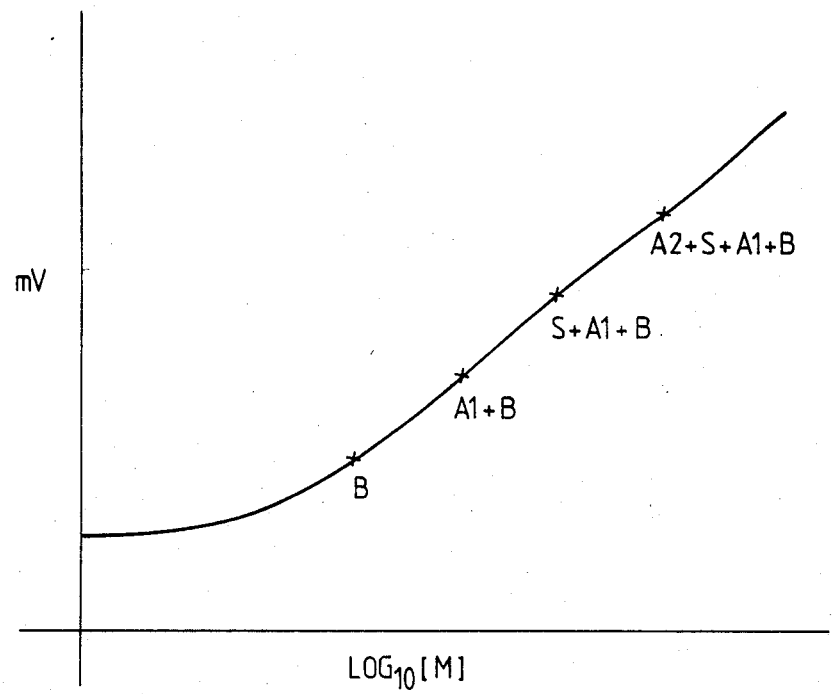
FIG. 2 is a curve representing the theoretical response of the ISE.

The basis for the method of the invention may be understood by reference to FIG. 2 which illustrates graphically the theoretical response curve of the ISE. The co-ordinate B for the base solution will be on the linear part of the response curve by virtue of the doping of the base solution with the ion to be measured. At this stage, the actual response curve of the ISE is assumed to coincide with the theoretical curve for the ISE type in question. Also, at this stage a value for the electrode potential will be known but the concentration of the base solution will not be known precisely.

Upon addition of the standard solution, a new co-ordinate $A_1+B$ results although its true concentration value is not precisely known. However, a value for the concentration of the base solution can be deduced from the theoretical response curve and hence the value of $A_1+B$ is determined.

The subsequent addition of the sample results in the co-ordinate $S+A_1+B$ from which, using the theoretical response curve, the concentration value of $S+A_1+B$ can be obtained. From this value and that obtained for co-ordinate $A_1+B$ the concentration of the sample can be readily deduced.

The foregoing procedure may be reduced to a mathematical routine in the form of a computer programme which is executed by the control unit 20. It will be noted that the concentration of the base solution need not be well-defined since it is derived from the theoretical response curve after the electrode potential has been obtained. Thus, it is not essential for the cell 10 to be rinsed or cleaned out after each measuring cycle.

As described above, the determination of the ion concentration of the sample involves the use of the theoretical response curve and does not allow for any possible departure of the actual response curve of the ISE from theoretical. However, any inaccuracies arising from this assumption can be eliminated by the expedient of adding to the cell 10 at least one additional standard and/or sample solution in the course of each measuring cycle. This further addition is depicted in FIG. 2 by the co-ordinate $A_2+S+A_1+B$ corresponding to the addition of a further standard solution which, for convenience, may have a greater concentration than the first standard to ensure that the co-ordinate $A_2$ is adequately separated from co-ordinate $S+A_1+B$ (bearing in mind the semilogarithmic nature of the response curve). By establishing at least four co-ordinates, it is not necessary to assume that the actual response curve of the ISE coincides precisely with the theoretical curve. In this case, the four co-ordinates may be treated in terms of four simultaneous equations which, collectively, contain four unknowns and can therefore be solved mathematically employing a suitable algorithm programmed into the control unit 20. In the most complicated situation, for example, for fluorine concentration in $UF_4$ and using the preferred multi-addition procedure, the equations are as follows:

For $B$,
$$y_1 = C_1 + C_2 \log_{10} \frac{C_3}{W - \text{(numerator)}}$$

For $A_1 + B$,
$$y_2 = C_1 + C_2 \log_{10} \frac{\frac{V}{V+v_1}[C_3 + (A_1 \times K_1)]}{W - \text{(numerator)}}$$

For $S + A_1 + B$,
$$y_3 = C_1 + C_2 \log_{10} \frac{\frac{V}{V+v_2}\left[C_3 + (A_1 \times K_1) + \left(\frac{S \times M_1 \times C_4}{100 \times M_2}\right)\right]}{W - \text{(numerator)}}$$

For $A_2 + S + A_1 + B$,
$$y_4 = C_1 + C_2 \log_{10} \frac{\frac{V}{V+v_3}\left[C_3 + (A_1 \times K_1) + \left(\frac{S \times M_1 \times C_4}{100 \times M_2}\right) + (A_2 \times K_2)\right]}{W - \text{(numerator)}}$$

where
- y1, y2, y3, y4 are the respective measured electrode potentials
- $C_1$ is the standard potential (mV)
- $C_2$ is the electrode slope (mV)
- $C_3$ is the base solution blank (g)
- $C_4$ is % w/w F in sample S
- V = vol of base solution (ml)
- v = cumulative vol of additions (ml)
- $A_1$ = weight of first addition (g)
- S = weight of sample addition (g)
- $A_2$ = weight of second addition (g)
- $K_1$ = concentration of first standard solution (gF/g)
- $K_2$ = concentration of second standard solution (gF/g)
- $M_1$ = weight of sample (g)
- $M_2$ = weight of sample solution (g)
- W = 0.19 (g fluorine equivalent to 50 ml 0.2M ferric solution on a 1:1 molar basis).

In the above equations, $C_1$, $C_2$, $C_3$ and $C_4$ are the unknowns although it will be observed that only three of the equations are needed if $C_2$ is assumed to be the theoretical slope. The term (numerator) in each equation is the same as the numerator in the same equation, ie in the equation for y3 the denominator will be $$W - \frac{V}{V+v_2}\left[C_3 + (A_1 \times K_1) + \left(\frac{S \times M_1 \times C_4}{100 \times M_2}\right)\right]$$

The parameter W in the denominator corrects approximately but adequately for the small but significant decreases in the ratio of total fluorine concentration to free fluorine ion concentration which occurs on making the additions to the base solution. In the absence of complexation the denominators in the four equations equal unity.

Computer programs for solving (SEQS) or fitting data to (NLLSQ) non-linear and other equations not readily amenable to manual solution and suitable for solving the above equations are available from CET Research Group Ltd, PO Box 2029, Norman, Okla. 73070, USA.

I claim:

1. A method of making an analysis of ion concentration in a series of samples using an ion-selective electrode in an electrode cell comprises the steps of:
   (a) filling the cell with an approximately known volume of base solution doped with a trace of the ion to be determined and taking an initial reading of the electrode output;
   (b) adding from a dispenser a volume of liquid (herein called the standard solution), containing a known concentration of the ion to be measured;
   (c) recording the changed electrode output;
   (d) adding a volume of the first sample for analysis, which value has a known proportional relation with said volume of standard solution;
   (e) recording the new electrode output;
   (f) draining the cell without rinsing;
   (g) proceeding back to (a) above for the next sample analysis; and
   (h) calculating the results of the analysis from the recorded values of the electrode outputs.

2. The method of claim 1 in which the additions in (b) and (d) are reversed.

3. A method as claimed in claim 1 in which more than one addition of standard solution and/or sample is made.

4. A method as claimed in claim 3 in which, for each sample, a set of at least four equations are obtained of the form $y_n = C_1 + C_2 f(M)$ where $n = 1, 2, 3, 4 \ldots$, $C_1$ corresponds to the standard potential of the ion selective electrode/reference electrode, $C_2$ corresponds to the electrode slope, f is a logarithmic function, y is the electrode potential obtained after each solution is added to the cell and M is related to the concentration of the cell contents at each stage in the procedure and on completion of the addition procedure includes contributions from the base solution and the sample addition(s), and in which the resulting equations for yn are solved to derive values for $C_1$, $C_2$ and the concentrations of the base solution and sample solution.

5. A method as claimed in claim 1 in which additions of standard solution are made prior to and after the addition of the sample.

6. A method as claimed in claim 5 in which the concentration of the standard solution added after the sample is greater than that of the standard solution added prior to the sample.

7. A method as claimed in claim 1 in which the volumes of the standard and sample solutions are all the same.

8. A method as claimed in claim 7 in which the standard and sample solutions are introduced by way of the same dispenser.

9. Apparatus for determining ion concentration in a series of samples, comprising an electrode cell, an ion selective electrode located in the cell, means for registering the output of the electrode, means for supplying an at least approximately known volume of a base solution to the cell, the base solution in use being doped with a trace of the ion with respect to which the electrode is selective, means for supplying to the cell a volume of liquid (herein called the standard solution) containing a known concentration of said ion, means for supplying to the cell one of said samples in a volume related to that of the standard solution, means for draining the contents of the cell, and control means for effecting cyclical operation of the registering means, the supplying means and the draining means in such a way that, during each cycle, the base solution is initially added to the cell and is followed by successive additions of the standard and sample solutions in a predetermined order, and finally the cell is drained, the next cycle being initated by adding base solution to the cell without an intermediate rinsing step, the registering means being operable to record the output of the electrode after each such addition to the cell and the draining means being operated to empty the cell in preparation for the next cycle, the control means including means for computing from said recorded outputs the ion concentration for each sample.

10. Apparatus as claimed in claim 9 in which each cycle involves the addition of at least two standard solutions and/or sample solutions.

11. Apparatus as claimed in claim 10 in which two standard solutions are added to the cell, one prior to and the second after the addition of the sample solution.

12. Apparatus as claimed in claim 9 in which the concentration of the second and any further addition of standard solution is greater than that of the first standard solution.

* * * * *